(12) United States Patent
Groves et al.

(10) Patent No.: US 6,448,239 B1
(45) Date of Patent: Sep. 10, 2002

(54) PEROXYNITRITE DECOMPOSITION CATALYSTS AND METHODS OF USE THEREOF

(75) Inventors: John T. Groves; Suzanne M. Moeller, both of Princeton, NJ (US)

(73) Assignee: Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/587,382

(22) Filed: Jun. 1, 2000

Related U.S. Application Data

(60) Provisional application No. 60/137,308, filed on Jun. 3, 1999.

(51) Int. Cl.$^7$ .................. A61K 31/555; C07D 487/22
(52) U.S. Cl. .................. 514/81; 514/185; 540/145
(58) Field of Search .................. 540/145; 514/81, 514/185

(56) References Cited

U.S. PATENT DOCUMENTS

| | | | | |
|---|---|---|---|---|
| 5,109,016 A | | 4/1992 | Dixon et al. ........... | 514/410 |
| 5,284,647 A | | 2/1994 | Niedballa et al. ....... | 424/81 |
| 5,663,393 A | * | 9/1997 | Jacobsen et al. ....... | 556/45 |
| 5,801,229 A | * | 9/1998 | Sessler et al. ......... | 534/15 |
| 6,002,026 A | | 12/1999 | Groves et al. ......... | 549/533 |
| 6,087,493 A | * | 7/2000 | Wheelhouse et al. ... | 540/145 |
| 6,103,714 A | | 8/2000 | Fridovich et al. ...... | 514/185 |
| 6,245,758 B1 | | 6/2001 | Stern et al. ........... | 514/185 |

FOREIGN PATENT DOCUMENTS

| | | |
|---|---|---|
| EP | 0 524 161 A1 | 1/1993 |
| WO | WO 93/16721 | 9/1993 |
| WO | WO 95/31197 | 11/1995 |

OTHER PUBLICATIONS

Jakobs et al., Chemical Abstracts, vol. 126:324503, 1997.*
Cheng et al., Chemical Abstracts, vol. 112:146393, 1990.*
Wu et al., Chemical Abstracts, vol. 113:143962, 1990.*
Wheelhouse et al., Chemical Abstracts, vol. 129:170516, 1998.*
Hunt et al., Chemical Abstracts, vol. 128:123775, 1997.*
Woehrle et al., Chemical Abstracts, vol. 123:354281, 1995.*
Tong et al., Chemical Abstracts, vol. 120:94146.*
Lee, et al., Bioorganic & Medicinal Chemistry Letters, 7:2913–2918 (1997).
Lee, et al., J. Am. Chem. Soc., 120:7493–7501 (1998).
Misko, et al., J. of Biol. Chem., 273:15646–15652 (1998).
International Search Report dated Dec. 13, 2000.
Hunt, J. A., Lee, J., Groves, J. T., Amphiphilic peroxynitrite decomposition catalysts in liposomal assemblies, Chem. Biol. 1997, 4 (11): 845–58.
Groves, J.T., Artificial Enzymes. The importance of being selective; Nature, 1997, 389: 329–30.
Groves, J.T., Peroxynitrite: reactive, invasive and enigmatic, Chem. Biol., 1999, 3:226–235.
Reedijk, J., Medicinal applications of heavy–metal compounds, Chem. Biol., 1999, 3:236–240.
Pasternack, R.F., et al., Solution Properties of Tetrakis–(4–N–Methyl)Pyridylporphineiron(III), J. Inorg. Nucl. Chem. 1977, 39: 1865–1870.

* cited by examiner

*Primary Examiner*—Richard L. Raymond
(74) *Attorney, Agent, or Firm*—Mintz, Levin, Cohn, Ferris, Glovsky and Popeo, PC; Ivor R. Elrifi, Esq.

(57) ABSTRACT

This invention provides a novel class of substituted macrocyclic metallic complexes. The complexes are useful as peroxynitrite decomposition catalysts. Pharmaceutical compositions, and methods of making and using the compounds, or a pharmaceutically acceptable salt, hydrate, prodrug, or mixture thereof are also described.

22 Claims, 6 Drawing Sheets

R = A, B, C, D = :

-(CH$_2$)$_n$-X where n=1 to 6 and X = -COOH; -CONH$_2$; -CONR$_2$; -O-PO$_3$H$_2$; -PO$_3$H$_2$; -SO$_3$H; -NH$_2$; -NR$_2$; -NR$_3^+$ -(CH$_2$)$_n$-Y where n = 2 to 6 and Y = -OH; -(-O-(CH$_2$)$_2$)$_m$- Y; m= 1 - 200

-(-O-(CH$_2$)$_2$)$_m$- X where m = 1 - 200 and X = as defined above

1.

Y$_2$ = -(CH$_2$)$_n$O-; -(CH$_2$)$_n$NH-; -(CH$_2$)$_n$S-

2.

3.

4.

5.

R = A, B, C, D = :

6.

7.

PEROXYNITRITE DECOMPOSITION CATALYSTS AND METHODS OF USE THEREOF

RELATED APPLICATIONS

This application claims priority to U.S. Ser. No. 60/137,308, filed Jun. 3, 1999. The contents of this application are incorporated herein by reference in their entirety.

FIELD OF THE INVENTION

The invention relates in general to substituted metallic complexes and more particularly to substituted porphyrin-, porphyrazine-, texaphyrin-, salen-, or corrole-metal complexes.

BACKGROUND OF THE INVENTION

The peroxynitrite ion ($ONOO^-$) is a potent oxidant formed by the combination of nitric oxide (NO) and the superoxide anion ($O_2$)$^-$. NO has been shown to be generated by numerous cell types, such as macrophages, neutrophils, hepatocytes and endothelial cells. The direct combination of NO with $O_2$ produces the peroxynitrite ion ($ONOO^-$), which decomposes rapidly under physiological conditions to oxidizing intermediates. These oxidizing intermediates can damage biological targets.

Pathological consequences associated with damage to biological targets can include the oxidizing or nitrating of proteins, lipids and DNA. $ONOO^-$ crosses lipid membranes at a rate significantly faster than the rates of other known oxidants, indicating that this oxidant can travel distances of cellular dimensions. Thus, even in the presence of biological membranes, $ONOO^-$ can have free access to cellular interiors. $ONOO^-$ is also known to nitrate tyrosine residues in proteins, and to oxidize sulfhydryls, methionines and macromolecules such as, for example, metalloenzymes, DNA, and lipids.

In light of this reactivity, $ONOO^-$ has been implicated in a variety of diseases. These diseases include, e.g., neurodegenerative disorders such as Alzheimer's disease, amyotrophic lateral sclerosis, stroke, AIDS dementia and Hungington's disease; heart diseases such as atherosclerosis; chronic inflammation and autoimmune diseases such as arthritis, inflammatory bowel disease, and acute respiratory disease syndrome; cancer; ischemia-reperfusion injury; septic shock; and chronic rejection of renal grafts.

SUMMARY OF THE INVENTION

The invention is based in part on the discovery of novel substituted metallic complexes that are effective peroxynitrite decomposition catalysts. Preferred catalysts have one or more of the properties of high catalytic activity, high stability and enhanced lifetime in the blood pool, advantageous tissue distribution, and low toxicity. The peroxynitrite decomposition catalysts can be used to treat a variety of conditions and diseases, including those known to involve the accumulation of the oxidant peroxynitrite.

Accordingly, in one aspect the invention provides a novel substituted metallic complex falling within one of formulas I through VII, as set forth in the Detailed Description of the Invention below. Compounds falling within the formula include various substituents, e.g., those including one or more polyethylene glycol (PEG) moieties.

Also provided are methods of treating neurodegenerative disorders, including Alzheimer's disease, amyotrophic lateral sclerosis, stroke, AIDS dementia and Hungington's disease; atherosclerosis; chronic inflammation; autoimmune diseases, including arthritis, inflammatory bowel disease, and acute respiratory disease syndrome; cancer; ischemia-reperfusion injury; septic shock; and chronic rejection of renal grafts in mammals by administering to a mammal in need of such treatment a pharmaceutically effective amount of a compound according to one of formulas I–VII.

In a further aspect, the invention also includes a method for the production of compounds according to any one of formulas I–VII.

Also provided are pharmaceutical compounds including the compounds of the invention and a pharmaceutically acceptable carrier.

In yet another aspect, the invention includes the use of compounds disclosed herein as diagnostic probes to determine the involvement of peroxynitrite and other reactive oxygen and nitrogen species in disease states both in vivo and in vitro.

The details of one or more embodiments of the invention are set forth in the accompanying description below. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

Figure 1:
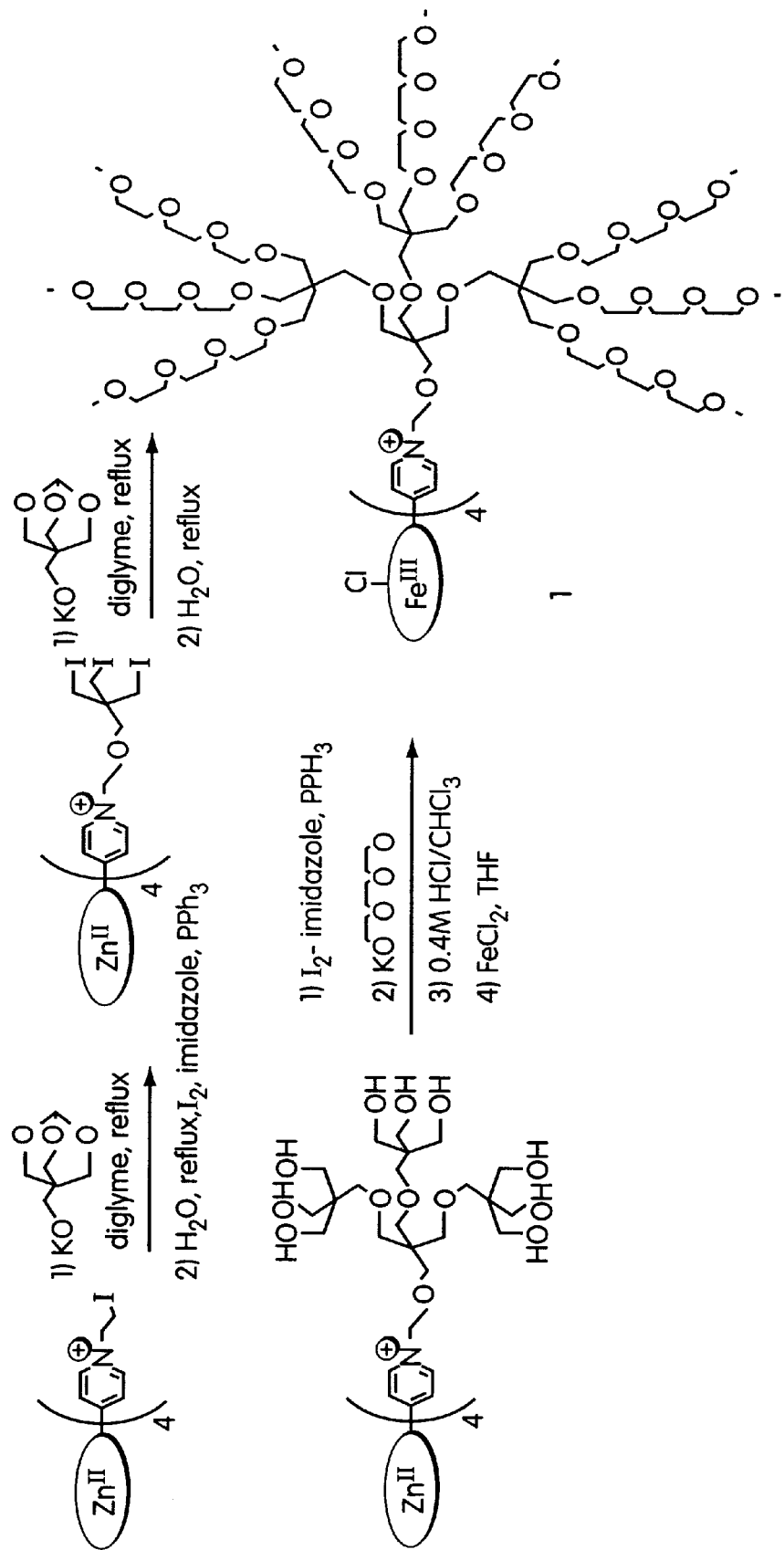
FIG. 1 is a schematic illustration of the preparation metalloporphyrin amphiphiles according to one embodiment of the invention.

The invention provides novel substituted macrocyclic ligands that can be complexed to a metal to form metallic complexes. The complexes are useful as e.g., peroxynitrite decomposition catalysts. In some embodiments, the metallic complexes include substituted porphyrin, porphyrazine, texaphyrin, salen, or corrole complexes.

The invention is based in part on the discovery that substituted 2-pyridyl-porphyrins are unexpectedly effective peroxynitrite decomposition catalysts. Substitutions in metallic complexes as described herein can result in increased biocompatibility, which can be characterized as producing at least one of the following effects: (1) enhancement of the $ONOO^-$ decomposition activity of the complex; (2) enhanced stability and half-life in vivo; (3) optimized tissue distribution throughout the body; and (4) lowered toxicity when administered to a subject. In some embodiments, the substituted amphiphilic macrocyclic ligands are present in liposomes.

Structures of Macrocyclic Ligands

Macrocyclic ligands can include, e.g., substituted 2- (Formula I) and 4- (Formula II) substituted TMPyps, substituted TMPSs, 2-, 3-, and 4-substituted pyridylporphyrazines, and substituted Texaphyrins, substituted corroles and substituted salens. Metal complexes with the substituted macrocyclic ligands according to the invention are shown below:

Formula I

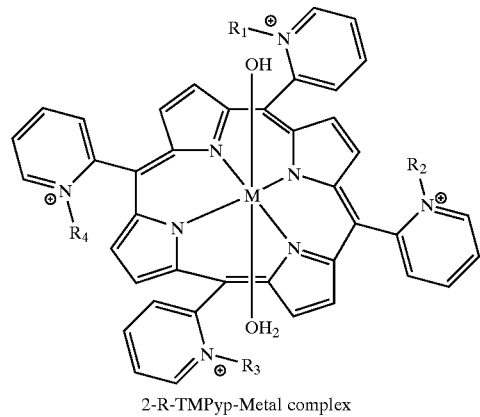

2-R-TMPyp-Metal complex

Formula II

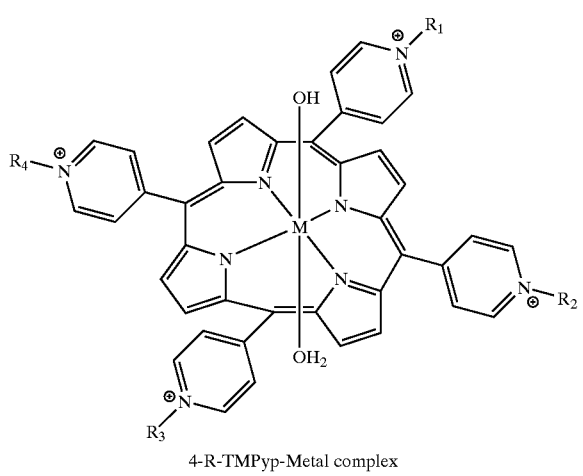

4-R-TMPyp-Metal complex

Formula III

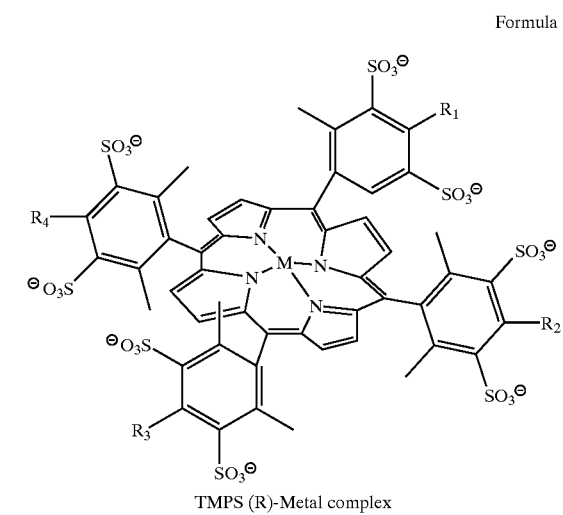

TMPS (R)-Metal complex

Formula IV

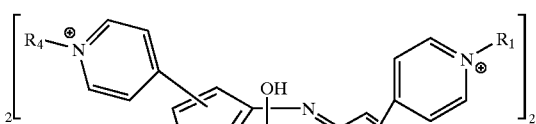

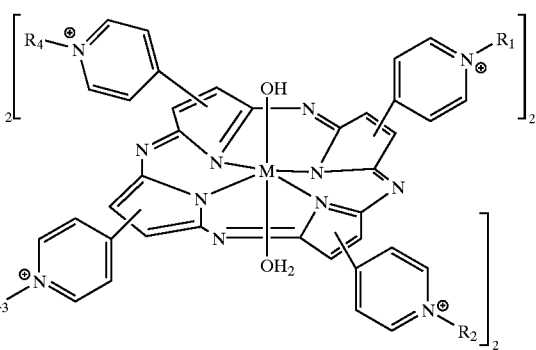

2-, 3-, and 4-R-pyridyl porphyrazine-Metal complexes

Formula V

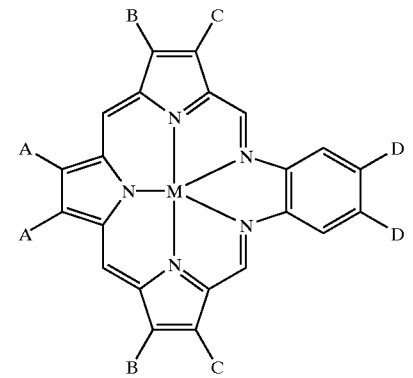

Texaphyrin-Metal complexes

Formula VI

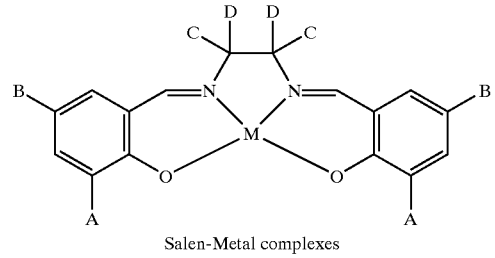

Salen-Metal complexes

Formula VII

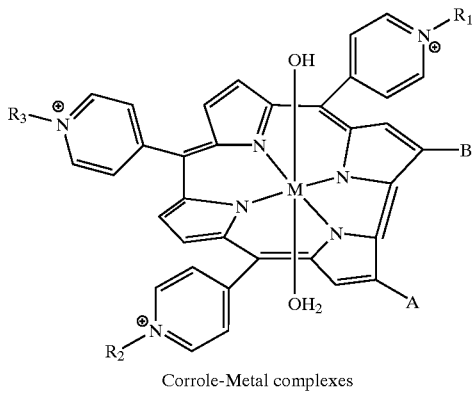

Corrole-Metal complexes

The invention also includes equivalents of the general formulas set forth above for the compounds, as well as the intermediates of the compounds that have the same general properties as these compounds. Also included are tautomers of the compounds, e.g., compounds wherein one or more of the various R groups are simple variations of the substituents as defined therein, or substituents which are a higher alkyl group than that indicated. In another example, anions having a charge other than 1, e.g., carbonate, phosphate, and hydrogen phosphate, can be used instead of anions having a charge of 1, so long as they do not adversely affect the overall activity of the complex. However, using anions having a charge other than 1 will result in a slight modification of the general formula for the complex set forth above.

The substituents at $R_1$, $R_2$, $R_3$, $R_4$, A, B, C, and D include, independently, those falling within the general structures shown in FIGS. 2A and 2B, and the structures described below.

In some embodiments, $R_1$, $R_2$, $R_3$, $R_4$, A, B, C, or D is $(CH_2)_n$—X, where n=1 to 6 and X=—COOH; —$CONH_2$; —$CONR'_2$; —$OPO_3H_2$; —$PO_3H_2$; —$SO_3H$; —$NH_2$; —$NR'_2$; —$NR'_3{}^+$.

In some embodiments, $R_1$, $R_2$, $R_3$, $R_4$, A, B, C, or D is $(CH_2)_n$—Y, where n=2 and Y=—OH; —(O—$(CH_2)_2)_m$—W; W is —OH or (O—$(CH_2)_2)_m$, and m=1–200.

In some embodiments, $R_1$, $R_2$, $R_3$, $R_4$, A, B, C, or D is $Y_2$—C—$(Z_1)_3$, where $Z_1$ is $CH_2OCH_2(CH_2)_n$—X or —Y, where $Y_2$=—$(CH_2)_nO$—; —$(CH_2)_nNH$—; —$(CH_2)_nS$—, and n=1 to 10.

In some embodiments, $R_1$, $R_2$, $R_3$, $R_4$, A, B, C, or D is $(CH_2)_n$—C(O)— $Y_2$—$C(Z_2)_3$, where $Z_2$ is —$CH_2$—O—$CH_2CH_2C(O)$—$Y_2$—$C(Z_4)_3$, where $Z_4$ is —$CH_2$—O—$CH_2CH_2Z_5$, where $Z_5$ is COOH; —$CONH_2$; $CONR'_2$; —$PO_3H_2$; —$SO_3H$; —$NH_2$; —$NR'_2$; or —$NR'_3{}^+$.

In some embodiments, $R_1$, $R_2$, $R_3$, $R_4$, A, B, C, or D is $(CH_2)_n$—O—$CH_2C(CH_2OH)_2CH_3$) or $(CH_2)_n$—O—$CH_2CH(CH_2OH)_2$ and n=1 to 10.

In some embodiments, $R_1$, $R_2$, $R_3$, $R_4$, A, B, C, or D is $(CH2)_n$—$OCH_2C(CH_2OH)_3$, and n=1 to 10.

$R_1$, $R_2$, $R_3$, $R_4$, A, B, C, and D can be independently selected from any of the foregoing substituents, and n=1 to 10.

In some embodiments, the compounds are provided in association with suitable ligands or charge neutralizing anions, denoted as X and Y. These can be derived from any monodentate or polydentate coordinating ligand or ligand system or the corresponding anion thereof. They are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl, amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isozutrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, alkyl aryl guanidino, alkyl carbamate, aryl carbamate, alkyl aryl carbamate, alkyl thiocarbamate, aryl thiocarbamate, alkyl aryl thiocarbamate, alkyl ditbiocarbamate, alkyl aryl dithiocarbamate, bicarbonate, carbonate, perchlorate, chlorate, chlorite, hypoclorite, perbromate, bromite, hypobromite, tetrahalomanganate, tetrafluororate, hexafluorophosphate, hexafluoroanitmonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems; with the proviso that when the X and Y containing complex has a net positive charge then Z' is a counter ion which is independently X or Y, or when the X and Y containing complex has net negative charge then Z' is a counter ion selected from a group consisting of alkaline and alkaline earth cations, cations, organic cations such as alkyl or akylaryl ammonium cations.

M is a metal, and is preferably selected from the group consisting of Mn, Fe, Ni and V.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxy-phenyl, 4-(tert-butoxy)phenyl, 4-fluorophenyl, 4-chiorophenyl, 4-hydroxyphenyl, 1-naphthyl, 2-naphthyl, and the like.

The term "aralkyl", alone or in combination, means an alkyl or cycloalkyl radical as defined herein in which one hydrogen atom is replaced by an aryl radical as defined herein, such as benzyl, 2-phenylethyl, and the like.

The term "heterocyclic" means ring structures containing at least one other kind of atom, in addition to carbon, in the ring. The most common of the other kinds of atoms include nitrogen, oxygen and sulfur. Examples of heterocycles include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "cycloalkyl", alone or in combination means a cycloalkyl radical containing from 3 to about 10, preferably from 3 to about 8, and most preferably from 3 to about 6 carbon atoms. Examples of such cycloalkyl radicals include, but are not limited to, cyclopropyl, cyclobutyl, cyclopentyl, cyclohexyl, cycloheptyl, cyclooctyl, and perhydronaphthyl.

The term "cycloalkenyl", alone or in combination, means a cycloalkyl radical having one or more double bonds. Examples include, but are not limited to, cyclopentenyl, cyclohexenyl, cyclooctenyl, cyclopentadienyl, and cyclooctadienyl.

The term "metal(s)" refers to any atom of the Periodic Table having the properties of a metal. These include preferably all transition metals, actinides and lanthanides. More preferably tin, silicon, germanium, copper, iron, cobalt, zinc, nickel or manganese are used. See *Porphyrins and Metalloporphyrins* by K. M. Smith, Elsevier/North-Holland Biochemical Press (1976), which is incorporated herein in its entirety by reference. "Metal salt" refers to an organic or inorganic salt used to treat a dihydro-porphyrin structure to produce the corresponding metal porphyrin compound. Acetates and propionates are preferred.

The term "pharmacologically effective amount" as used herein means an amount that slows or prevents the progression of the targeted disease or pathology. It is preferable that the slowing or prevention not be accompanied by a toxic effect that offsets the medical value of slowing or preventing the progression of the targeted disease or pathology.

The "pharmaceutically acceptable carrier" must be "acceptable" in the sense of being compatible with the compounds or compositions of the invention and not deleterious to the subject to be treated. Preferably, the carrier is also capable of stabilizing the compound or composition.

Salts encompassed within the term "pharmaceutically acceptable salts" refer to non-toxic salts of the compounds of this invention which are generally prepared by reacting the free base with a suitable organic or inorganic acid to produce "pharmaceutically-acceptable acid addition salts" of the compounds described herein. These compounds retain the biological effectiveness and properties of the free bases. Representative of such salts are the water-soluble and water-insoluble salts, such as the acetate, amsonate (4,4-diaminostilbene-2,2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

In some embodiments, the metallic complex is based on a porphyrin structure. As used herein, the term "porphyrin" includes derivatives wherein a metal atom is inserted into the ring system, as well as molecular systems in which ligands are attached to the metal. The substituents, as well as the overall porphyrin structure, can be neutral, positively charged, or negatively charged.

Figure 2A:
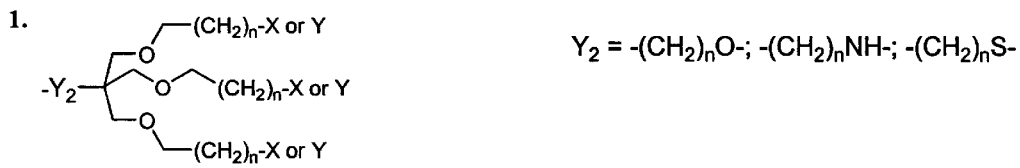
FIGS. 2A and 2B are illustrations of substituent groups for macrocylic ligands according to the invention.
Figure 2A:
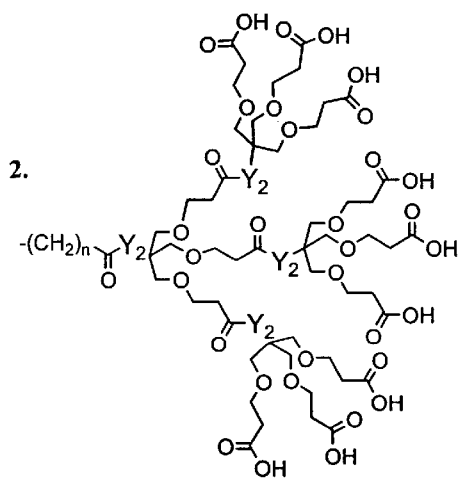
Figure 2A:
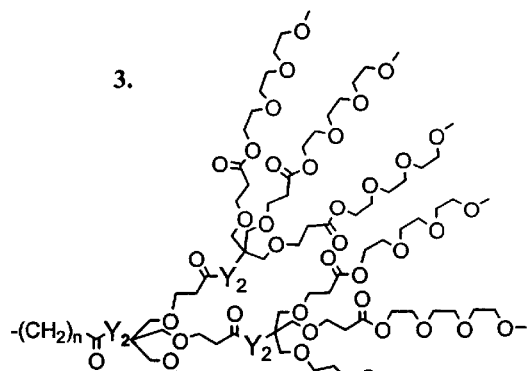
Figure 2A:
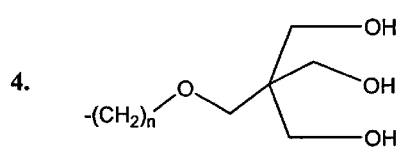
Figure 2A:
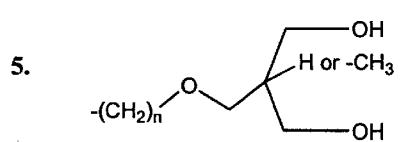
Figure 2B:
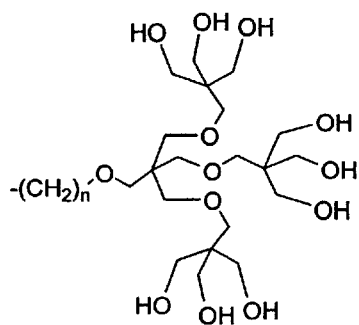
Figure 2B:
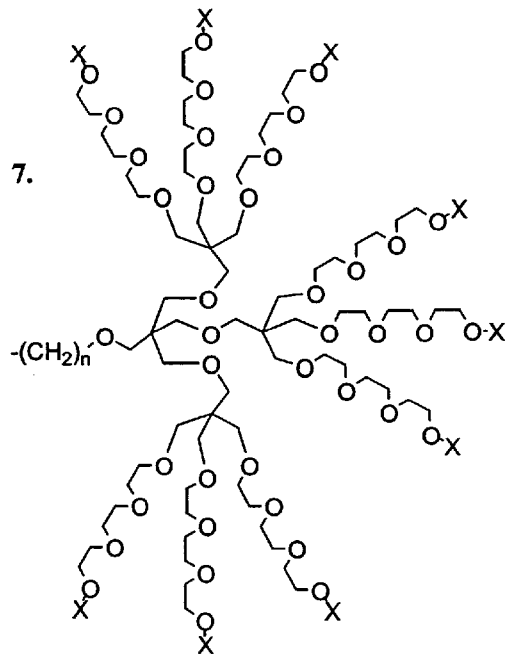

As is shown in FIGS. 2A and 2B, various substituent groups can vary in length according to the numbers of polyethylene glycol (PEG) groups included. In some embodiments, a $(CH_2)_n$—NHCO motif or a $(CH_2)_n$—CONH motif, where n=1 to 100, can be linked to an amino acid motif, a peptide motif, or a polypeptide motif. In some embodiments, the motif can be linked to a region of a polypeptide that is a targeting sequence.

In some embodiments, the invention includes compounds having the formula (VIII), tetrakis (allyl-2-pyridyl) porphyrin; (IX), tetrakis (acetamido-2-pyridyl)porphyrin; (X), tetrakis (ethylaceto-2-pyridyl)porphyrin; and (XI), tetrakis (triethylene glycol monomethyl ether-2-pyridyl) porphyrin. For each (VIII)–(XI) shown, R and X are as indicated.

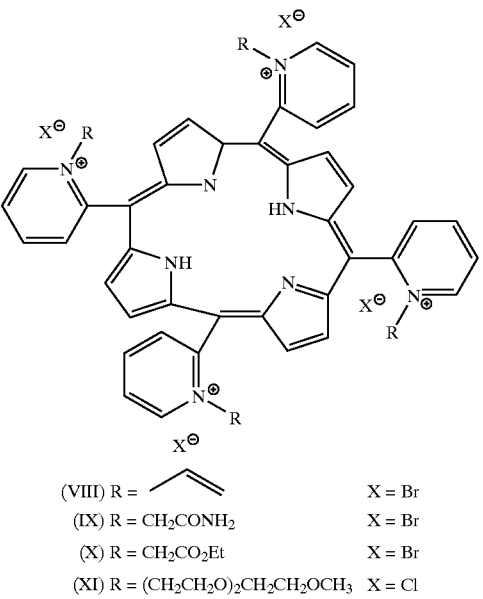

(VIII) R = —CH=CH₂    X = Br
(IX) R = CH₂CONH₂    X = Br
(X) R = CH₂CO₂Et    X = Br
(XI) R = (CH₂CH₂O)₂CH₂CH₂OCH₃    X = Cl

Synthesis of Peroxynitrite Decomposition Catalysts

In various embodiments, the macrocyclic ligands of the invention are provided as a metallic complex. The complexes can be, e.g., porphyrin-, porphyrazine-, texaphyrin-, salen-, or corrole-metal complexes.

Starting porphyrins, porphyrazines, texaphyrins, salens, or corroles can be prepared accordind to methods well known in the art. The methods can include, for example, those described in WO95/31197, Campestrini and Meunier, and Inorg. Chem. 31, 1999–2006, (1992); Robert et al., Inorg. Chem. 30, 706–711, (1991); Lindsey and Wagner, J. Org. Chem. 54, 828–836, (1989); and Zipplies, et al., J. Am. Chem. Soc. 108, 4433–4445, (1986). See, also, Meltze; Phthalocyanine Technology in Chemical Process Reviews No. 42.; Noyes Data Corp. Park Ridge, N.J. (1970). See, also, Goedken, et al., J.C.S. Chem. Comm. 337–338, (1973); Martin, and Cummings, Inorg. Chem. 12, 1477–1482, (1973); Riley, et al., J. Am. Chem. Soc. 98, 1752–1762, (1976); Dabrowiak, et al., J. Am. Chem. Soc. 95, 6613–6622, (1973); Riley and Busch, Inorg. Chem. 23, 3235–3241, (1984); Watkuns, et al., Inorg. Chem. 15,387–393, (1976); and Riley, et al., J. Am. Chem. Soc. 99, 767–777, (1977).

Salens can be prepared according to methods described by e.g., Diehl and Hoch, Inorganic Synthesis Vol. 3. p 196. McGraw-Hill, New York (1950); Srinivasan, et al., J. Am. Chem. Soc. 108, 2309–2320, (1986); and Samsel, et al., J. Am. Chem. Soc. 107, 7606–7617, (1985).

In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

Pyridinium porphyrins can also be synthesized as described in Hunt et al., in Chem. & Biol. 4:845–58, 1997.

Synthesis of Amphiphilic Catalysts and Preparation of Vesicular Assembly Systems According to the Invention The invention includes amphiphilic complexes containing a metallic complex, e.g., a porphyrin complex. Porphyrin complexes can be synthesized as described generally in Hunt et al., in Chem. & Biol. 4:845–58, 1997. A general synthetic scheme for preparing substituted metallic complex amphiphiles within the invention is also presented in FIG. 1. Shown is a scheme for preparing polyether cascade dendritic porphyrins. The depicted synthesis results in a symmetrical solution dendrimer. If desired, unsymmetrical derivatives with a single hydrophobic side chain can be readily prepared by procedures known in the art. While not wishing to be bound by theory, it is believed the side chains lower toxicity by minimizing or preventing liver uptake, thereby allowing the catalyst to be maintained longer in a subject's blood pool. If desired, targeting agents such as steroids can be attached.

Amphiphilic metallic complex analogs can include end products synthesized using procedures generally described Hunt et al., in Chem. & Biol 4:845–58, 1997. For example, iron and manganese porphyrins can be constructed by using as starting materials pyridium porphyrins that are synthesized according to methods known to those skilled in the art and referenced above. For example, these pyridium porphyrins can be synthesized by peralkylation of 5, 10, 15, 20,-tetrakis(4-pyridyl)porphine with an appropriate alkyl iodide, e.g., dodecyl iodide.

Porphyrins preferably are located in a hydrophilic environment for the efficient catalysis of peroxynitrite. Thus, in preferred embodiments, the invention includes PEG-linked (polyethylene glycol) substituted porphyrins. In certain aspects of the invention, these porphyrins can be provided in vesicular assemblies, such as liposomes. In such an environment, the PEG-linkers extend the metalloporphrin headgroup away from the interfacial region between the membrane and external solution and further into the bulk solvent. The hydrophilicity of the porphyring headgroup correlates with the efficiency of the catalysts: the rate of peroxinitrite decomposition is much faster when catalyzed by PEG-linked metalloporphyrins, as compared to metalloporphyrins with simple dodecyl chains. In some embodiments, tocopherol, e.g., α tocopherol or, preferably, γ tocopherol, is also present in the vesicular assembly.

The compounds can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, including by formation of diastereoisomeric salts through treatment with an optically active acid (e.g., tartaric, diacetyltartaric, dibenzoyltartaric, ditoluoyltartaric and camphorsulfonic) and then separation of the mixture of diastereoisomers by crystallization followed by liberation of the optically active bases from these salts. Another process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The chemical reactions shown by the references described above are generally disclosed in terms of variations appropriate for their broadest application to the preparation of the metallic complexes of this invention. Occasionally, the reactions may not be applicable as described to each metallic complex included within the disclosed scope. The metallic complexes for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, or the like. Alternatively, other reactions disclosed herein or otherwise conventionally known, will be applicable to the preparation of the corresponding metallic complexes of this invention. In all preparative methods, all starting materials are known or readily preparable from known starting materials.

Additional methods for synthesizing catalysts according to the invention are described in the Examples, below.

Screening Macrocyclic Ligands for Catalytic Activity

To screen metal complexes for peroxynitrite decomposition catalytic activity of the invention, peroxynitrite is prepared and isolated as its sodium salt by the reaction of acidic hydrogen peroxide with sodium nitrite followed by rapid quenching with NaOH as set out by Halfpenny and Robinson, in *J. Chem. Soc.*, 928–938 (1952). Peroxynitrite has an absorbance maximum at 302 nm with an extinction coefficient of 1670 $M^{-1}cm^{-1}$. Therefore, it is possible to directly observe the decomposition of peroxynitrite by monitoring the change in absorbance at 302 nm by stop-flow spectrophotometric analysis. For example, the decomposition of peroxynitrite at an accelerated rate (relative to the natural decomposition rate of peroxynitrite) upon the addition of the decomposition catalysts of the invention.

In addition, it is known that peroxynitrite inactivates CuZn—SOD (superoxide dismutase) enzyme in a concentration dependant manner. Peroxynitrite is also reported to inactivate Mn—SOD. See Ischiropoulos et al., *Archives of Biochemistry and Biophysics*, 298:2, 431–437 (1992). The invention provides compounds and methods for screening for compounds which protect CuZn—SOD or Mn—SOD by inactivating peroxynitrite.

Peroxynitrite catalytic activity can also be measured using methods described in Hunt et al., Chem. & Biol. 4:845–58, 1997.

Pharmaceutical Compositions

The pharmaceutical compositions of the invention include a pharmaceutically effective amount of one or more of the metallic complexes of the invention administered in a dosage regimen appropriate for treating a disease condition. The dosage regimen is selected in accordance with a variety, of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

For example, total daily dose administered to a mammal in single or divided doses may be in amounts, for example, from about 1 to about 100 mg/kg body weight daily and more usually about 3 to 30 mg/kg. Dosage unit compositions may contain such amounts of submultiples thereof to make up the daily dose. The number of submultiples is preferably about one to three times per day of about 30 mg/kg per unit dosage form. The serum concentrations of the doses are about 1 pM to 1.5 $\mu$M, e.g., 3 pM–1.0 $\mu$M, 300 pM to 750 nM, 500 pM to 250 nM, or 1 nm to 125 nM. Furthermore, the amount of active ingredient that may be combined with the carrier materials to produce a single dosage form will vary depending upon the host treated and the particular mode of administration.

The invention also includes pharmaceutical compositions suitable for decomposing peroxynitrite in a cell both in vivo and in vitro. More preferably, the invention includes pharmaceutical compositions suitable for decomposing peroxynitrite under physiological conditions. The compositions are preferably suitable for internal use and include an effective amount of a pharmacologically active compound of the invention, alone or in combination, with one or more pharmaceutically acceptable carriers. The compounds are especially useful in that they have very low, if any toxicity.

In practice, the metallic complexes of the inventions or their pharmaceutically acceptable salts, are administered in amounts which will be sufficient to inhibit inflammatory conditions or disease and/or prevent the development of inflammation or inflammatory disease in animals or mammals, and are used in the pharmaceutical form most suitable for such purposes.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient. Administration of the active metallic complexes of the inventions and salts described herein can be via any of the accepted modes of administration for therapeutic agents. These methods include systemic or local administration such as oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active metallic complexes of the invention or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active metallic complexes of the invention may be also formulated as suppositories using for example, polyalkylene glycols, for example, propylene glycol, as the carrier.

Liquid, particularly injectable compositions can, for example, be prepared by dissolving, dispersing, etc. The active metallic complexes of the invention is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection. One approach for parenteral administration employs the implantation of a slow-release or sustained-released systems, which assures that a constant level of dosage is maintained, according to U.S. Pat. No. 3,710,795, incorporated herein by reference.

The metallic complexes of the invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the metallic complex desired can be employed as an antiandrogenic agent.

The dosage regimen utilizing the metallic complexes is selected in accordance with a variety of factors including type, species, age, weight, sex and medical condition of the patient; the severity of the condition to be treated; the route of administration; the renal and hepatic function of the patient; and the particular metallic complex or salt thereof employed. An ordinarily skilled physician or veterinarian can readily determine and prescribe the effective amount of the drug required to prevent, counter or arrest the progress of the condition.

Oral dosages of the invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the metallic complexes of the invention range from 0.002 mg to 50 mg per kg of body weight per day.

Metallic complexes of the invention may be administered in a single daily dose, or the total daily dosage may be administered in divided doses of two, three or four times daily. Furthermore, preferred metallic complexes for the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The metallic complexes herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The metallic complexes of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Metallic complexes of the invention may also be delivered by the use of monoclonal antibodies as individual carriers to which the metallic complex molecules are coupled. The metallic complexes of the invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the metallic complexes of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. Any of the above pharmaceutical compositions may contain 0.1–99%, preferably 1–70% of the active metallic complexes, especially metallic complexes of the Formula I as active ingredients.

While the metallic complexes of the invention can be administered as the sole active pharmaceutical agent, they can also be used in combination with one or more metallic complexes of the invention or with one or more metallic complexes which are known to be effective against the specific disease state that one is targeting for treatment.

Therapeutic Methods

The invention also provides methods for preventing or reducing cellular damage resulting from exposure to various chemical compounds which produce potentially damaging free radical species, comprising administering a therapeutically or prophylactically efficacious dosage of at least one species of a substituted compound of the invention, e.g., a substituted metalloporphyrin.

Compositions including the herein described compounds may be administered for various indications, including: (1) for preventing ischemic reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens, and (6) for prophylactic administration to prevent: carcinogenesis, cellular senescence, cataract formation, formation of malondialdehyde adducts, HIV pathology and macromolecular crosslinking, such as collagen crosslinking. In one aspect of the invention, ligand-metal complexes (e.g., metalloporphyrins) are formulated for administration by the oral route by forming a pharmaceutical dosage form comprising an excipient and not less than 1 microgram nor more than about 10 grams of at least one antioxidant complex of the invention. Dietary formulations are administered for therapy of free radical-induced diseases and/or for the chemoprevention of neoplasia and/or oxidative damage associated with normal aerobic metabolism.

In another aspect, buffered aqueous solutions comprising one or more antioxidant substituted metallic complex, e.g., a substituted metalloporphyrin, at a concentration of at least 1 nM but not more than about 100 mM is formulated for administration, usually at a concentration of about 0.1 to 10 mM, to a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application, (2) antineoplastic or antihelminthic chemotherapy employing a chemotherapeutic agent which generates free radicals, (3) endotoxic shock or sepsis, (4) exposure to ionizing radiation, (5) exposure to exogenous chemical compounds which are free radicals or produce free radicals, (6) thermal or chemical burns or ulcerations, (7) hyperbaric oxygen, or (8) apoptosis of a predetermined cell population (e.g., lymphocyte apoptosis). Administration can be via any desired route, e.g., intravenous, subcutaneous, inhalation, intramuscular. The buffered aqueous solutions may also be used, typically in conjunction with other established methods, for organ culture, cell culture, transplant organ maintenance, and myocardial irrigation. Nonaqueous formulations, such as lipid-based formulations are also provided, including stabilized emulsions. The invention also encompasses pharmaceutical compositions of ligand-metal complexes, therapeutic uses of such complexes, methods and compositions for using these complexes in diagnostic, therapeutic, and research applications in human and veterinary medicine.

Another aspect of the invention is its use in enhancing the recovery of skin of a warm-blooded animal from wounds, such as surgical incisions, burns, inflammation or minor irritation due to oxidative damage, etc. This method includes administering to the skin wound or irritation a therapeutically or, in some cases a prophylactically effective amount of a composition which comprises a substituted metal complex, e.g. a substituted metalloporphyrin, as described herein. Additionally, the invention provides a method of treating a peroxide-induced condition in a subject which comprises administering to the subject an amount of any of the compounds of the invention effective to reduce peroxide in a subject and thereby treat the peroxide-induced condition. Administration of the compound to the subject may be effected by means other than those listed herein. Further, the peroxide-induced condition may involve cataracts, inflammation of a tissue, ischemia, an allergic reaction, or pathology caused by oxidative stress. Where the peroxide-induced condition involves cataracts, administration is effected by, but is not limited to, topical contact to the surface of an eye.

The method includes contacting the cell with any compound of formulas I–VII (or, e.g., formulae VIII–XI) in a pharmaceutically effective amount, that is, sufficient to actively decompose peroxynitrite in the cell. In general, any cell having peroxynitrite, or capable of synthesizing peroxynitrite, can be treated. The cell can be provided in any form so long as it is accessible to the compound. For example, the cell can be provided in vitro, ex vivo, or in vivo. Peroxynitrite decomposition can be measured using any method known in the art, e.g., methods such as stopped-flow kinetic analysis.

Also provided in the invention is a method of inhibiting, preventing, or treating a pathology advantageous affected by the decomposition of peroxynitrite in a mammal. The disease or pathology can be associated, e.g., with an inflammatory disease or neurodegenerative disease characterized by the presence of peroxynitrite. Inflammatory diseases refer to diseases or conditions where there is an inflammation of the body tissue. Neurodegenerative diseases refer to diseases causing the breakdown of neural tissue and/or function. These both include local inflammatory responses and systemic inflammation. Examples of such diseases and conditions include: transplant rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gum, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis and viral or autoimmune encephalitis; autoimmune diseases including diabetes mellitus, immune-complex vasculitis, systemic lupus erythematosus (SLE); inflammatory diseases of the heart such as cardiomyopathy, ischemic heart disease, hypercholesterolemia, and atherosclerosis; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines.

The invention also includes a method of treating, preventing, or otherwise inhibiting reperfusion injury in a subject in need of treatment, prevention, or inhibition thereof. The method includes administering a peroxynitrite decomposition catalyst as disclosed herein in an amount sufficient to inhibit reperfusion injury in the subject. Reperfusion refers to the process whereby blood flow in the blood vessels is resumed after blood flow has been interrupted, such as occurs following constriction or obstruction of the vessel. Reperfusion is typically associated with ischemia and may result following a naturally occurring episode, such as a myocardial infarction or stroke, or during a surgical procedure where blood flow in vessels is purposely or unintentionally blocked off.

The subject in the above-mentioned methods can be, e.g., a mammal, e.g., a human, mouse, rat, dog, cat, horse, cow, pig, or non-human primate. Administration can be systemic or topical, and can be prophylactic or therapeutic.

The invention will be further described in the following examples, which do not limit the scope of the invention described in the claims.

EXAMPLE I

Synthesis of Tetrakis (Allyl-2-pyridyl)porphyrin (VIII)

In an oven-dried flask under argon, 100 mg tetrakis(2-pyridyl)porphyrin (2-PyP) was dissolved in 5 mL allyl bromide, and reaction was heated at 100° C. for 16 hours. The reaction mixture was heated at 100° C. for 8 hours. Two methods were used to monitor the completion of the reaction. First, the shift of the porphyrin Soret band from $\lambda_{max}$=412 nm (methanol) to $\lambda_{max}$=418 nm (methanol) was monitored. A second method involved partition of an aliquot of the reaction mixture between $H_2O$ and $CHCl_3$ whereby a complete reaction showed no color in the $CHCl_3$ layer. Upon completion of the reaction, the allyl bromide was distilled off under high vacuum, and the residue was triturated with ethyl ether ($Et_2O$). Chromatography was performed on Sephadex LH-20 (column dimensions were 2×20 cm) using methanol as the eluent and fractions that showed porphyrin with $\lambda_{max}$=418 nm were retained. Compound VIII was produced as a shiny purple solid, in 78% yield. Absorbance data included the following: UV-vis: $\lambda_{max}$ (nm) ($\log_{10}\epsilon_o$) 418(5.29) 512 (4.50) 587(4.32). Electrospray mass spectrometry (ES-MS) showed a molecular ion at 782 (M–4 Br).

EXAMPLE II

Synthesis of Compound (IX): Tetrakis (Acetamido-2-pyridyl)porphyrin

In an oven-dried flask under argon, 50 mg 2-PyP was added to 1.0 g bromoacetamide and 2.5 mL dry DMF. The reaction mixture was heated at 100° C. for 8 hours. The reaction was monitored as above. Compound IX was isolated by dropping the completed reaction mixture into $Et_2O$ and precipitating the resulting solid from methanol/Et$_2$O. The solid was filtered and washed well with CHCl$_3$ and Et$_2$O. Chromatography on Sephadex LH-20 (column dimensions 2×15 cm) using methanol as the eluent and by collecting the fastest-running red band produced (IX) in 75% yield. Absorbance data included the following: UV-Vis: $\lambda_{max}$ (nm) (log$_{10}\epsilon_o$) 418(5.20) 512(4.27) 587(4.01). ES-MS: Molecular ion at 850 (M−4 Br).

EXAMPLE III

Synthesis of Compound (X): Tetrakis (Ethylaceto-2-pyridyl)porphyrin

To an oven-dried flask under argon was added 10 mg 2-PyP, 1 mL ethyl bromoacetate, and 2 mL dry DMF. The reaction mixture was heated at 100° C. for 6 hours. The reaction was monitored by the shift in the porphyrin Soret band from $\lambda_{max}$=412 nm (methanol) to $\lambda_{max}$=420 nm (methanol), and, by, partition of an aliquot of the reaction mixture between H$_2$O and CHCl$_3$ where a complete reaction showed no color in the CHCl$_3$ layer. When the reaction mixture was cooled to room temperature, some of the desired porphyrin precipitated out of solution. The remainder of product was precipitated from the reaction mixture by addition of Et$_2$O, and precipitate was filtered and washed well with CHCl$_3$ and Et$_2$O. The brown solid was precipitated from methanol/Et$_2$O and filtered to give compound (X), as purple crystals, in 75% yield. Absorbance data included the following: UV-vis: $\lambda_{max}$ (nm) (log$_{10}\epsilon_0$) 420 (5.29) 512(4.46) 555(4.30) 585(4.28). ES-MS: molecular ion at 966 (M−4 Br).

EXAMPLE 4

Synthesis of Compound (XI): Tetrakis (Triethylene Glycol Monomethyl Ether-2-pyridyl)porphyrin To an oven-dried flask under argon was added 100 mg 2-PyP, 2 g. triethylene glycol monomethyl ether p-toluenesulfonate, and 4 ML dry DMF. The reaction mixture was heated at 80° C. for 2 days. The reaction mixture was then heated at 100° C. for 8 hours. Reaction was monitored by the shift in the porphyrin Soret band from $\lambda_{max}$=412 nm (methanol) to $\lambda_{max}$=418 nm (methanol), and by partition of a colorless aliquot of the reaction mixture between H$_2$O and CHCl$_3$ into the CHCl$_3$ layer. Porphyrin was isolated by adding the reaction mixture to 10 mL H$_2$O and precipitating with ammonium hexafluorophosphate, then filtering precipitate onto Celite. Porphyrin was washed off the Celite with acetone and was precipitated from acetone with tetrabutylammonium chloride. In some instances, the red gummy precipitate was again filtered onto Celite, washed well with acetone, then washed off the Celite with methanol. Chromatography of the porphyrin on Sephadex LH-20 using methanol as the eluent and collection of appropriate fractions yielded compound (XI), a gummy red solid, in 86% yield. Data included the following: ES-MS: a molecular ion at 1206 (M−4 Cl).

EXAMPLE 5

Iron and Manganese Metallations of Alkylated 2-Pyridyl Porphyrins

Iron metallations were performed according to the procedure of Pastemack et al.(J. Inorg. Nucl. Chem., 1977, 39, 1865–1870). Typically, 50 mg of free base was refluxed with an 5 to 10-fold excess of ferrous ammonium sulfate in 5–10 mL water. The reaction was monitored by UV-vis, and was considered complete when the Soret band of the free base ($\lambda_{max}$=418) had shifted to approximately $\lambda_{max}$=412. Furthermore, upon successful alkylation, the number of Q-bands decreased from four to two. NMR spectra also showed a very characteristic shift of the pyrrole protons from δ=9–10 ppm to δ=90–95 ppm. The reaction was complete in 2–6 hours. Yield ranged from 50–80%, depending on ease of isolation. The iron porphyrins were typically purified by chromatography on Sephadex LH-20. No satisfactory mass spectral data could be obtained for any of these porphyrins.

Manganese metallations were performed by refluxing the free base with a 2-fold excess of Mn(OAc)$_2$. Typically, 50 mg of free base was reacted with Mn(OAc)$_2$ in 5–10 mL water. The reaction was monitored by UV-vis, and was considered complete when the Soret band ($\lambda_{max}$=412) had shifted to $\lambda_{max}$=447. In addition, two shoulders appeared in the spectrum. The porphyrins were purified by chromatography on Sephadex LH-20, and yields were typically 85–90%.

EXAMPLE 6

Peroxynitrite Decomposition Activity for FeCl T(PEG3)PyP.

Figure 3:
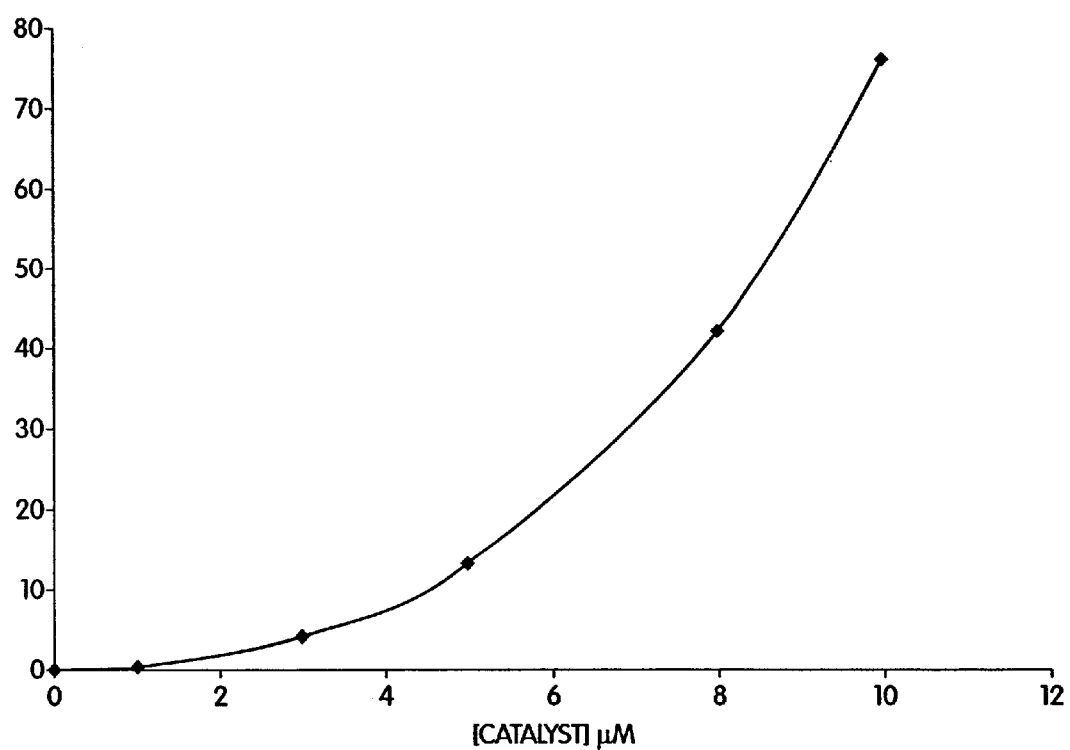
FIG. 3 is a representation of graph showing rates of reaction between peroxynitrite and Fe-T(PEG$_3$)PyP.

High rates of peroxynitrite decomposition is an important indicator of biological activity in vitro and in vivo. The rates of reaction between peroxynitrite and FeCl T(PEG$_3$)PyP were measured at several different concentrations of catalyst in phosphate buffer (pH=7.4. ) The results are presented in FIG. 3. The k$_{cat}$ was measured to be at least $7.9 \times 10^6$ M$^{-1}$s$^{-1}$, the detection limit of the stopped-flow instrument. This is the highest value yet recorded for such a catalyst. Other 2-alkylpyridyl porphyrins in this series gave similar rates.

In addition to high rates of peroxynitrite decomposition, the 2- and 4-pyridylporphyrin agents gave typically >95% nitrate and very little nitrite as decomposition products, as determined by Gries Reagent titrations. This is a significant result, since low nitrite is indicative of low nitrogen dioxide produced from the peroxynitrite. Since protein nitration is a typical damaging effect of peroxynitrite, high levels of nitrate and low levels of nitrite indicate decreased protein nitration and enhanced cytoprotection by a given agent.

EXAMPLE 7

DNA Binding and Cleavage Studies

The degree to which peroxynitrite decomposition agents bind and cleave DNA provides an indication of the cellular toxicity of the agents. The studies detailed below indicated that while the 4-pyridyl porphyrins bind significantly to calf-thymus DNA (indicated by the characteristic shift in the visible spectrum), the corresponding 2-pyridyl porphyrins do not show such binding. Further, upon treatment with oxidants such as hydrogen peroxide, oxone or peroxynitrite, the 2-pyridyl porphyrins caused much less DNA cleavage, as indicated by monitoring the conversion of closed circular plasmid DNA to open circular and linear forms.

Figure 4:
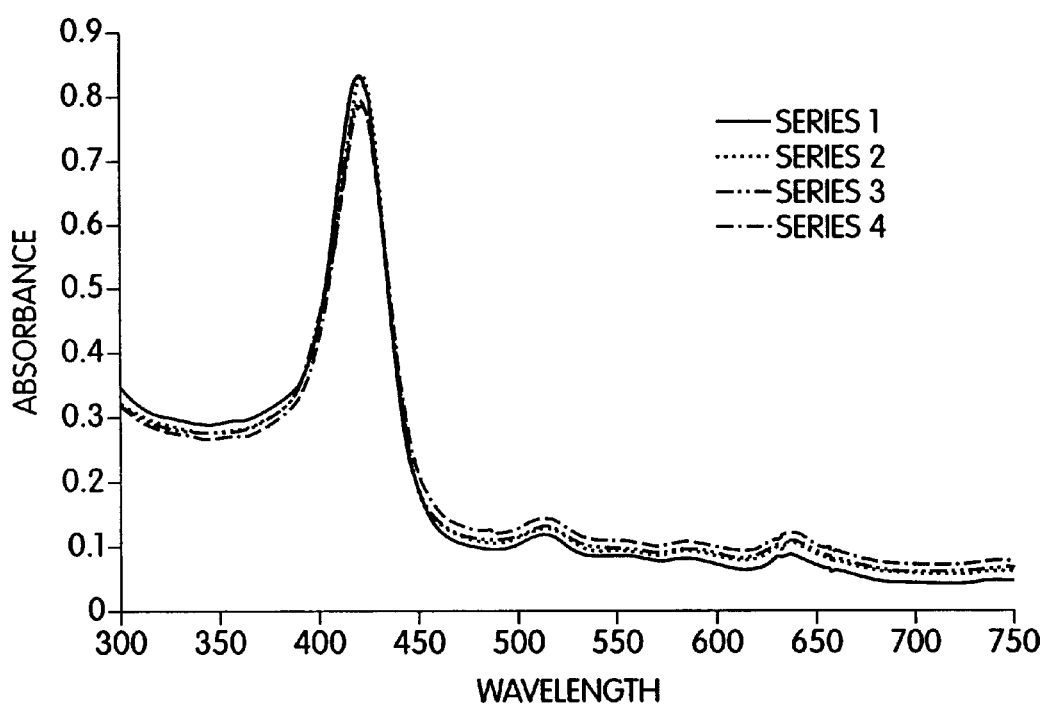
FIG. 4 is a representation of absorbance spectra obtained for calf thymus DNA in the presence of for 2-T(CX)PyP.

Calf thymus-DNA Titration of T(CX)PyP
Titration of 4-Tetrakis(carboxamide)pyridyl Porphyrin (4-T(CX)PyP):
A 5 μM solution of 4-T(CX)PyP was prepared in 10 mM tris buffer+1 mM EDTA (pH=8.0). To 2 mL of this solution in a quartz cuvette, 1 μL aliquots of a 1.89 mM solution of calf thymus DNA (CT-DNA) in 10 mM tris+1 mM EDTA were added. The concentration of CT-DNA was determined by UV-visible spectrum. After each addition, the cuvette was vortexed to ensure good mixing, and the UV-visible spectrum was recorded. This procedure was repeated until no further significant changes were observed in the spectrum. Results of this titration are presented in FIG. 4. Several intermediate spectra were omitted for clarity.

In the case of 4-T(CX)PyP, the loss of intensity in the Soret band (%hypochromicity) and the pronounced redshift ($\Delta\lambda_{max}$=12 nm) is indicative of both porphyrin intercalation into DNA and outside stacking of porphyrin along the DNA backbone. The binding constant of 4-T(CX)PyP to DNA was calculated from this titration to be $7.99\times10^6$. Since the planar structure of 4-T(CX)PyP offers little steric hindrance to prevent association with DNA, this result is expected.

The porphyrin 2-T(CX)PyP was titrated in an analogous way to 4-T(CX)PyP, as described above. In this case, only a small change in the Soret band was observed, which indicates little or no association with DNA. Presumably, the ortho carboxamide groups provide sufficient steric bulk to prevent association of the positively-charged pyridyl groups with the negatively-charged sugar phosphate backbone. Even when CT-DNA was added in large excess to the solution of porphyrin, a redshift of only 2 nM was observed.

Cleavage of Plasmid DNA with Manganese Pyridyl Porphyrins

Manganese derivatives of pyridyl porphyrins are known to cleave single-stranded DNA. Assaying the DNA-cleaving ability of the manganese derivatives of 2-alkylated pyridyl porphyrins according to the invention gives a clearer picture of the porphyrins' association with DNA, as well as the level of cytotoxicity in vivo that can be expected from the compounds.

The 2-PyP derivatives Mn(III) 4-tetrakis(carboxamide) pyridyl porphyrin (Mn 4-(CX)PyP); Mn(III) 2-tetrakis (carboxamide)pyridyl porphyrin (Mn 2-(CX)PyP); and Mn(III) 2-tetrakis(triethylene glycol monomethyl ether) pyridyl porphyrin (Mn 2-T(PEG$_3$)PyP) were assayed. The known DNA cleaving agent Mn 4-TMPyP was used as a standard.

Three forms of plasmid DNA are expected when Mn porphyrins interact with and cleave DNA, and they can be easily separated on an agarose gel. Uncleaved, supercoiled plasmid (Form I) will show the greatest mobility. In the event of a nick in the DNA, the supercoils will relax, and the open circular form of the plasmnid (Form II) will appear. Further oxidation will cleave the second strand of DNA as well, and leads to a linear form (Form III.) The relative electrophoretic mobilities are as follows: I>III>II.

The plasmid pBR322, a common cloning vector, was used. Oxone was used as the oxidant instead of ONOO, since its concentration is more easily regulated and it is more stable at room temperature and pH 7.4. Two concentrations of oxidant were used: 10 mM and 25 mM. All experiments were performed in 40 mM tris buffer+100 mM NaCl. Plasmid was obtained as a 500 μg/mL solution from Amersham Pharmacia Biotech. Before reaction, porphyrin was allowed to incubate with plasmid for 30 min.

A typical reaction was performed as follows: to a solution of 1 mM manganese porphyrin and 50 μg/mL plasmid in buffer was added enough oxone to make a final concentration of 10 mM or 25 mM. (Volume of the entire reaction was 20 μL.) The reaction mixture was vortexed, then allowed to react for 5 min. HEPES buffer (100 mM) was added to stop the reaction.

Figure 5:
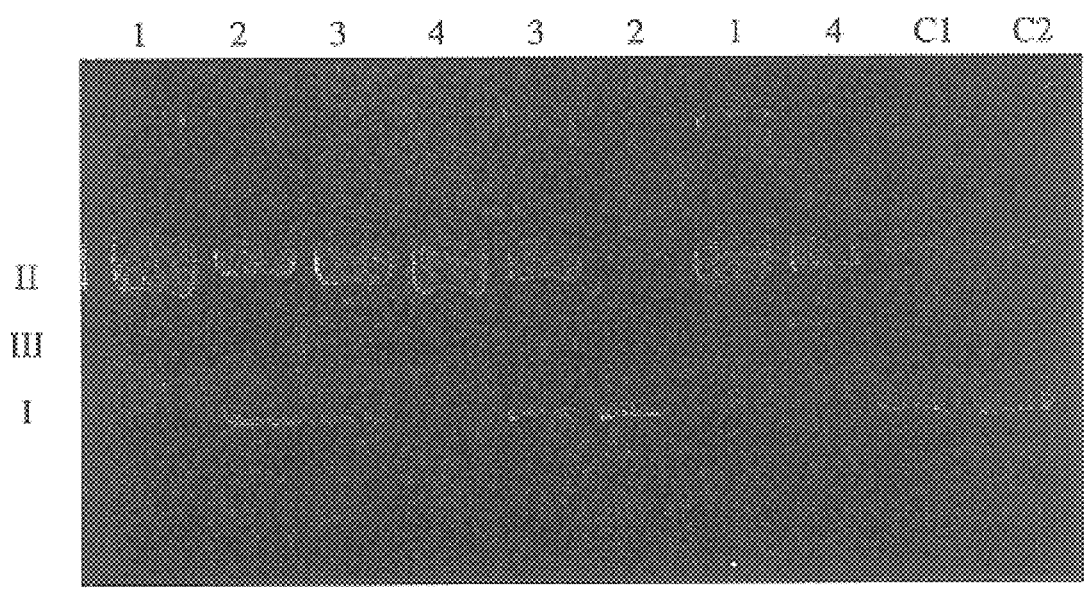
FIG. 5 is a representation of an electrophoretic analysis of topoligical forms of plasmid pBR322 in the presence of various substituted porphyrins.

Each sample was electrophoresed on a 1% agarose slab horizontal gel at 90V for 1 h at 24° C. in 40 mM tris-acetate (TAE) and 1 mM ETDA buffer. The agarose gel contained ethidium bromide (1 μg/mL) so that the lanes could be visualized by UV-vis, and the finished gel was photographed under UV illumination. The results of such an analysis are shown in FIG. 5. Lanes 1–4 were run at 10 mM oxone, and lanes 5–8 were run at 25 mM oxone. The control lanes, C1 and C2, contained 10 mM and 25 mM oxone, respectively, but no porphyrin. No plasmid cleavage was observed in these lanes, which served as a negative control. The lane assignments include the following: lane 1: Mn 4-T(CX)PyP, lane 2: Mn 2-T(CX)PyP; lane 3, Mn 2-T(PEG3)PyP; lane 4: Mn 4-TMPyP; lane C1: plasmid+10 mM oxone; lane C2: Plasmid+25 mM oxone The gel shown in FIG. 5 reveals that the greatest degree of plasmid cleavage took place in lanes containing 1 and 4. All four porphyrins nicked DNA to some extent, but the lanes containing 2-PyP derivatives showed significantly less nicking than the 4-PyP derivatives even at higher concentrations of oxidant. Furthermore, the linear form of DNA (Form III) does not appear at all in any lane containing 2 or 3. These results indicate that the these 2-PyP's do not cleave DNA efficiently.

OTHER EMBODIMENTS

It is to be understood that while the invention has been described in conjunction with the detailed description thereof, the foregoing description is intended to illustrate and not limit the scope of the invention, which is defined by the scope of the appended claims. For example, 2-pyridyl derivatives, particularly those including PEG substituents, are particularly advantageous as peroxynitrite decomposition catalysts. Other aspects, advantages, and modifications are within the scope of the following claims.

What is claimed is:

1. A metallic complex of Formula I:

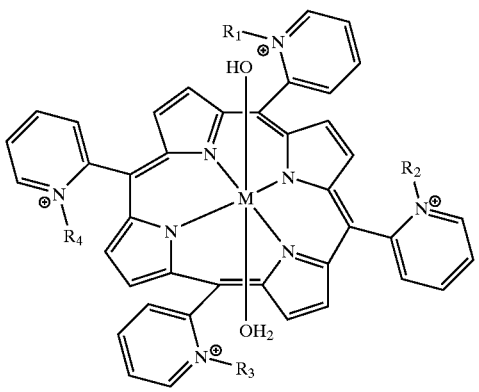

Formula I or a pharmaceutically acceptable base or acid addition salt, hydrate, ester, solvate, prodrug, metabolite, stereoisomer, or mixtures thereof, wherein at least one of $R_1$, $R_2$, $R_3$, or $R_4$, is independently selected from a moiety selected from the group consisting of:

—(CH$_2$)$_n$—X;

—(CH$_2$)$_n$—Y,

—CH$_2$CH=CH$_2$;

—CH$_2$CH$_2$OCH$_2$CH$_2$OCH$_2$CH$_2$OCH$_3$;

—CH$_2$CO$_2$CH$_2$CH$_3$;

—(OCH$_2$CH$_2$)$_m$—X;

—Y$_2$C(Z$_1$)$_3$, wherein: $Z_1$ is $CH_2OCH_2(CH_2)_nX$ or $CH_2OCH_2(CH_2)_nY$; —$(CH_2)_nC(O)Y_2C(Z_2)_3$, wherein: $Z_2$ is $CH_2OCH_2CH_2C(O)Y_2C(Z_4)_3$, $Z_4$ is $CH_2OCH_2CH_2Z_5$, and $Z_5$ is $CO_2(CH_2CH_2O)_m$, —COOH; —$CONH_2$; —$CONR'_2$; —$OPO_3H_2$; —$PO_3H_2$; —$SO_3H$; —$NH_2$; —$NR'_2$; or —$NR'^+_3$;

—$(CH_2)_nOCH_2C(CH_2OH)_3$;

—$(CH_2)_nOCH_2CH(CH_2OH)_2$;

—$(CH_2)_nOCH_2C(CH_2OH)_2(CH_3)$;

—$(CH_2)_nOCH_2C[CH_2OCH_2C(CH_2OH)_3]_3$; and

—$(CH_2)_nOCH_2C[CH_2OCH_2C(CH_2O[CH_2CH_2O]_mCH_2CH_2OX)_3]_3$, wherein n is an integer from 1 to 10; m is an integer from 1 to 200;

X is —COOH; —$CONH_2$; —$CONR'_2$; —$OPO_3H_2$; —$PO_3H_2$; —$SO_3H$; —$NH_2$; —$NR'_2$; or —$NR'^+_3$, further wherein R' is an alkyl group;

Y is —OH or —(O—$CH_2CH_2)_m$—W; where W is —OH, or —(O—$CH_2CH_2)_m$;

$Y_2$ is selected from the group consisting of —$(CH_2)_nO$—, —$(CH_2)_nNH$—, and —$(CH_2)_nS$—; and wherein the remaining $R_1$, $R_2$, $R_3$, and $R_4$ are hydrogen, and M is Mn or Fe.

2. The complex of claim 1, wherein at least two of $R_1$, $R_2$, $R_3$, or $R_4$ include said moiety.

3. The complex of claim 1, wherein at least three of $R_1$, $R_2$, $R_3$, or $R_4$ include said moiety.

4. The complex of claim 1, wherein four of $R_1$, $R_2$, $R_3$, or $R_4$ include said moiety.

5. The complex of claim 4, wherein the at least four moieties are identical.

6. The complex of claim 1, wherein said moiety is selected from the group consisting of —$CH_2CH=CH_2$, $CH_2CONH_2$, $CH_2CO_2CH_2CH_3$, and $CH_2CH_2OCH_2CH_2OCH_2CH_2OCH_3$.

7. The complex of claim 1, wherein said moiety is $CH_2CH=CH_2$.

8. The complex of claim 5, wherein $R_1$, $R_2$, $R_3$, and $R_4$ are $CH_2CH=CH_2$.

9. The complex of claim 1, wherein said moiety is $(CH_2)_nCONH_2$, where n is an integer from 1 to 6.

10. The complex of claim 1, wherein said moiety is $CH_2CONH_2$.

11. The complex of claim 5 wherein $R_1$, $R_2$, $R_3$, and $R_4$ are $CH_2CONH_2$.

12. The complex of claim 1, wherein said moiety is $CH_2CO_2CH_2CH_3$.

13. The complex of claim 5, wherein $R_1$, $R_2$, $R_3$, and $R_4$ are $CH_2CO_2CH_2CH_3$.

14. The complex of claim 1, wherein said moiety is $CH_2CH_2OCH_2CH_2OCH_2CH_2OCH_3$.

15. The complex of claim 5, wherein $R_1$, $R_2$, $R_3$, and $R_4$ are $CH_2CH_2OCH_2CH_2OCH_2CH_2OCH_3$.

16. A complex of formula I:

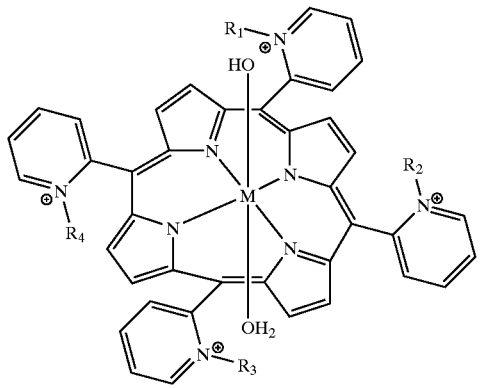

Formula I wherein $R_1$, $R_2$, $R_3$, or $R_4$ is selected from the group consisting of $CH_2CH=CH_2$, $CH_2CONH_2$, $CH_2CO_2CH_2CH_3$, and $CH_2CH_2OCH_2CH_2OCH_2CH_2OCH_3$, and M is Mn, or Fe.

17. A pharmaceutical composition comprising the complex of claim 16 and a pharmaceutically acceptable carrier.

18. A pharmaceutical composition comprising the complex of claim 1 and a pharmaceutically acceptable carrier.

19. A method of lowering peroxynitrite levels in a cell or tissue, the method comprising contacting said cell or tissue with a complex of claim 1 in an amount sufficient to lower peroxynitrite levels in said cell or tissue.

20. A method of treating or inhibiting the development of a pathology associated with peroxynitrite damage in a subject, the method comprising administering to a subject in need thereof a therapeutically effective amount of the complex of claim 1.

21. The method of claim 20, wherein said pathology is selected from the group consisting of Alzheimer's disease, amyotrophic lateral sclerosis, stroke, AIDS dementia, Huntington's disease, atherosclerosis; chronic inflammation; autoimmune diseases cancer, ischemia-reperfusion injury; septic shock, chronic graft rejection.

22. The method of claim 20, wherein said subject is a human.

* * * * *

UNITED STATES PATENT AND TRADEMARK OFFICE
CERTIFICATE OF CORRECTION

PATENT NO. : 6,448,239 B1
DATED : September 10, 2002
INVENTOR(S) : John T. Groves and Suzanne M. Moeller It is certified that error appears in the above-identified patent and that said Letters Patent is hereby corrected as shown below:

Column 1,
Line 4, insert the following:
-- STATEMENT AS TO FEDERALLY SPONSORED RESEARCH
This invention was made with Government support under NIH Grant No. 5 R01 GM36298 and the Government therefore has certain rights in this invention. --

Signed and Sealed this

Eleventh Day of February, 2003

JAMES E. ROGAN
*Director of the United States Patent and Trademark Office*